United States Patent [19]
Lundin

[11] Patent Number: 5,241,971
[45] Date of Patent: Sep. 7, 1993

[54] EAR-PROTECTION CUP FOR EAR MUFFS OR HEAD-PHONES

[75] Inventor: Rune Lundin, Värnamo, Sweden

[73] Assignee: Peltor Aktiebolag, Sweden

[21] Appl. No.: 784,779

[22] Filed: Oct. 30, 1991

[30] Foreign Application Priority Data

Nov. 2, 1990 [SE] Sweden .................................. 9003501

[51] Int. Cl.⁵ .............................................. A61F 11/14
[52] U.S. Cl. .................................... 128/864; 128/867; 381/183
[58] Field of Search ............... 128/846, 857, 864, 866, 128/867, 858, 859, 865, 868; 2/2, 410, 423; 381/183, 188, 189

[56] References Cited

U.S. PATENT DOCUMENTS

| 1,312,493 | 8/1919 | Theis ..................................... 128/866 |
| 3,102,538 | 9/1963 | Cowan .................................. 128/866 |

FOREIGN PATENT DOCUMENTS

| 3441120 | 5/1986 | Fed. Rep. of Germany ...... 128/866 |
| 3441122 | 5/1986 | Fed. Rep. of Germany ...... 128/867 |
| 1187815 | 10/1985 | U.S.S.R. .............................. 128/866 |
| 862136 | 3/1961 | United Kingdom ................ 128/866 |
| 9015584 | 12/1990 | World Int. Prop. O. ........... 128/867 |

*Primary Examiner*—Robert A. Hafer
*Assistant Examiner*—Sam Rimell
*Attorney, Agent, or Firm*—Ostrolenk, Faber, Gerb & Soffen

[57] ABSTRACT

An ear-protection cup for ear muffs or headphones comprising a cup-shaped frame and a resilient sealing member located at the peripheral edge thereof, by means of which the ear-protection cup can be brought into abutment with an annular shaped part of a user's head located around the ear. The frame is composed of a rigid, cup-shaped outer shell and an inner wall spaced from the outer shell and extending for a substantial way between the inner parts of the outer shell to which it is rigidly connected. The inner wall thus defines between itself and the outer shell an intermediate space in which a layer of elastomeric material is arranged compressed between the outer shell and the inner wall.

10 Claims, 3 Drawing Sheets

EAR-PROTECTION CUP FOR EAR MUFFS OR HEAD-PHONES

BACKGROUND OF THE INVENTION

The present invention relates to an ear-protection cup, for ear muffs or headphones, intended to be worn over the ears of a subject as protection against ambient noise and as an aid to wireless communication.

Ear protection cups of the type described above are known in the art, and are in present use. An example of this is found in the U.S. Pat. to Lienard, No. 2,684,067 which discloses a construction combining in a unitary structure a plurality of layers of metallic and non-metallic materials, having high coefficients of internal friction and having widely dissimilar moduli of elasticity. The layers are given a shape which permits the ready conformation of the device to the head of the wearer.

While ear-protection devices known in the art such as the one described above, substantially reduce external noise, such reduction is incomplete and, therefore, should be improved. The principal advantages of the present invention over the known prior art are the reduction of disturbing ambient noise, especially of ambient noise at higher frequencies.

OBJECTS OF THE INVENTION

An ear-protection cup is provided for protection against ambient noise, having a cup-shaped frame and a resilient sealing member located at the peripheral edge of the frame for abutting the cup with an annular shaped part of a user's head located around the ear. The frame is composed of a rigid, cup-shaped outershell and an inner wall spaced from the outer shell. The inner wall extends for a substantial way between the inner parts of the outer shell and defines space between its main part and the outer shell. The inner wall is rigidly connected to the inner parts of the outer shell and a layer of elastomeric material is arranged between the outer shell and the inner wall which exert pressure on the elastomeric material.

Due to the construction of the frame, external noise which may give rise to a wave pattern and, consequently, vibration in the outer shell will be dampened considerably more efficiently than would be the case if the frame consisted in the manner of a single shell. The reason for this seems to be that the two shells, since they have different dimensions and therefore different oscillatory patterns, will vibrate differently, the oscillatory movements thereby interfering with each other and being dampened mechanically by the intermediate layer of compressed elastomeric material. The outer shell thus has greatly reduced freedom to perform oscillatory movements and will therefore exert a higher reflective influence on the sound coming from outside. Furthermore, part of the sound will be converted to heat in the elastomeric material which acts on the whole as a sound trap since the sound entering has to travel further material during its passage towards the perforations in the inner shell.

In this case the inner shell may be provided with stiffening flanges in order to achieve an enhanced difference in oscillatory pattern (frequency charateristic) between the two shells.

According to another embodiment of the invention the inner shell is provided with a number of throughopenings arranged therein.

According to a preferred embodiment of the invention the intermediate gap between the outer and inner shells, filled with the elastomeric material, has a depth of 1–3 mm.

The layer of elastomeric material is suitably compressed to less than one half, preferably to less than one quarter of its thickness in an unloaded state in order to achieve strong mechanical suppression of the oscillatory motion in the two shells.

In order to achieve direct acoustic communication between the space between the two shells and the space within the inner shell, the inner shell is provided with sound passages as mentioned previously, e.g. in the form of throughopenings which may advantageously consist of perforations. Such an embodiment of the ear-protection cup increases its ability to achieve good suppression of even low-frequency sound despite the reduced free space inside the outer shell caused by the presence of the inner shell.

According to yet another embodiment of the invention the inner wall consists of a substantially flat wall extending between the inner sides of the outer shell and is spotwise attached to the outer shell by means of spacers, the inner wall in this case being suitably arranged to carry a headphone.

It is a primary object of the invention to provide an ear-protection cup as described which gives improved dampening of disturbing ambient noise with relatively high frequency, e.g. about 2000 Hz or more, in comparison with previously known ear-protection cups of similar type.

It is a further object of the invention to provide an ear-protection cup which is of simple construction, is light and convenient to wear, and is secure and safe in use.

It is a further object of the invention to provide an ear-protection cup which may be easily and inexpensively formed and assembled from predominantly plastic materials.

A further object of the invention is to provide an ear-protection cup that carries a headphone, and shields the audio signals from the headphone from external noise.

Various other objects and advantages of the invention will become more fully apparent from the following detailed description, in conjunction with the drawings, of two embodiments of the invention.

DESCRIPTION OF THE PREFERRED EMBODIMENTS

Figure 1:
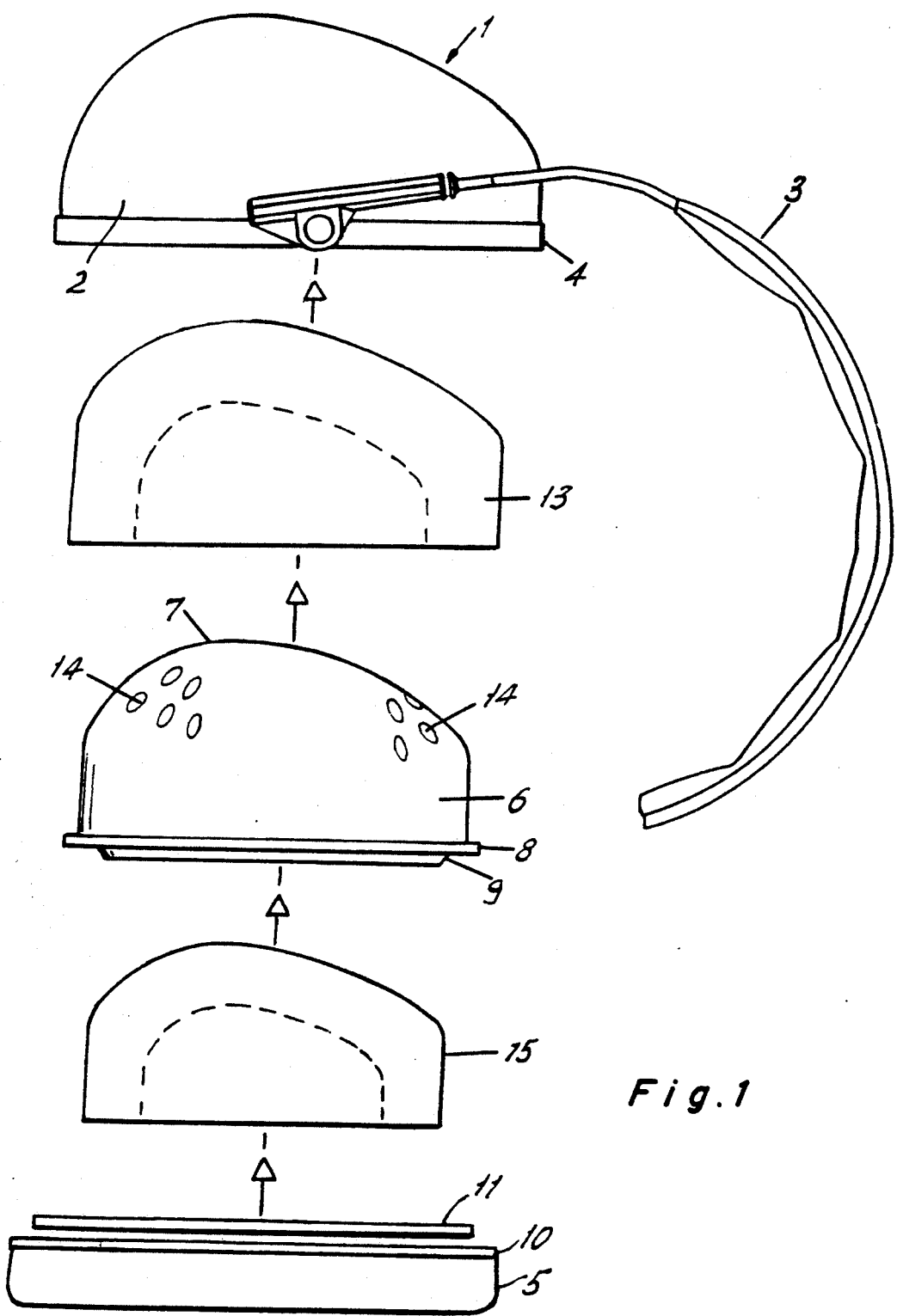
FIG. 1 shows an exploded view of one cup of an ear muff of a first embodiment of the invention.

One ear-protection cup of an ear muff is generally designated as 1 in the drawings.

The cup 1 comprises a substantially cup-shaped, rigid outer shell 2 comprised of a suitable plastic material, for instance. The cup 1 is flexibly attached in conventional manner to the end of a headband 3 and is provided at its peripheral edge 4 with a resilient sealing ring 5 intended to be in contact with the wearer's head.

Figure 2:
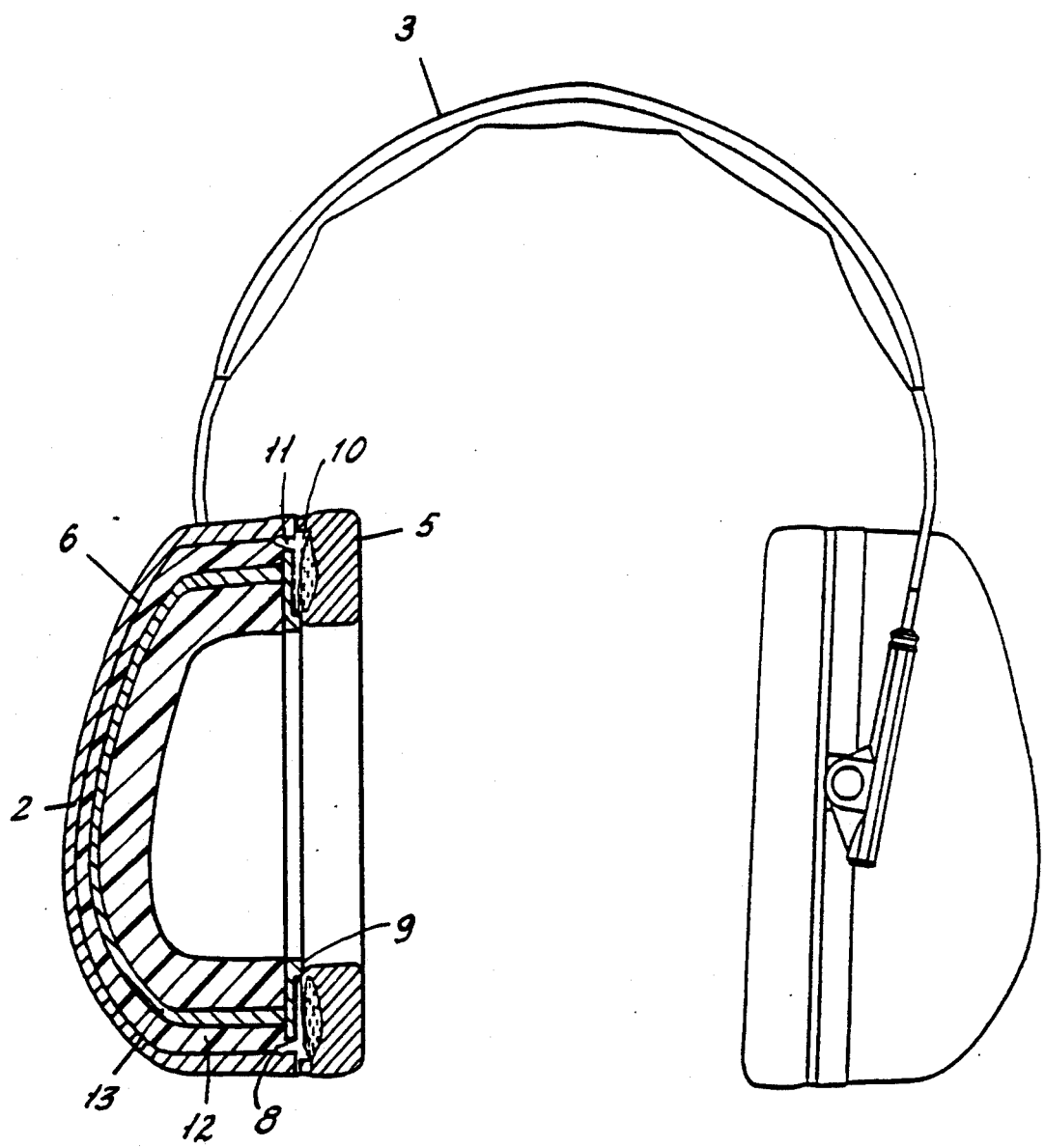
FIG. 2 shows an ear muff arrangement, the cup according to FIG. 1 being shown in cross-section.

In the embodiment illustrated in FIGS. 1 and 2 the cup 1 comprises a cup-shaped rigid inner wall in the form of a hollow body 6. The outer part 7 of the body 6, facing the outer shell 2, has suitably the same external contour as the internal contour of the outer shell 2.

The opposite, open end of the cup 6 is provided with a peripheral flange 8 protruding therefrom, and an annular shoulder 9 by means of which, when the cup is inserted into the outer shell, it is clamped between the latter and the outer sealing ring 5 which is provided with corresponding peripheral protrusions 10, 11.

When the cup 6 is inserted into the outer shell 2, a gap 12 is formed in which an insert 13 of elastomeric shall be arranged. Insert 13, when inserted, fills out the space 12 under compression from the outer shell 2 and the inner wall 6. In the embodiment shown in FIGS. 1 and 2 tne gap between the outer shell and the inner wall is only a few millimeters wide, e.g. 1-3 mm.

The elastomeric material used for the insert 13 should be compressible to more than one half and preferably more than one quarter of its thickness in an unloaded state. Certain foam plastics and the like are suitable for the elastomeric material.

The cup 6 illustrated is suitably provided with a number of through-openings 14.

The interior of the cup 6 may suitably be provided with a dampening filler material 15 of suitable cellular structure.

The insert 13 of elastomeric material compressed between the outer shell 2 and the cup 6 functions as a sound trap and creates a considerably longer path for the sound from the outer shell to travel through the elastomeric material to the perforations in the inner shell. A part of this sound will also be converted to heat in the elastomeric material.

Figure 3:
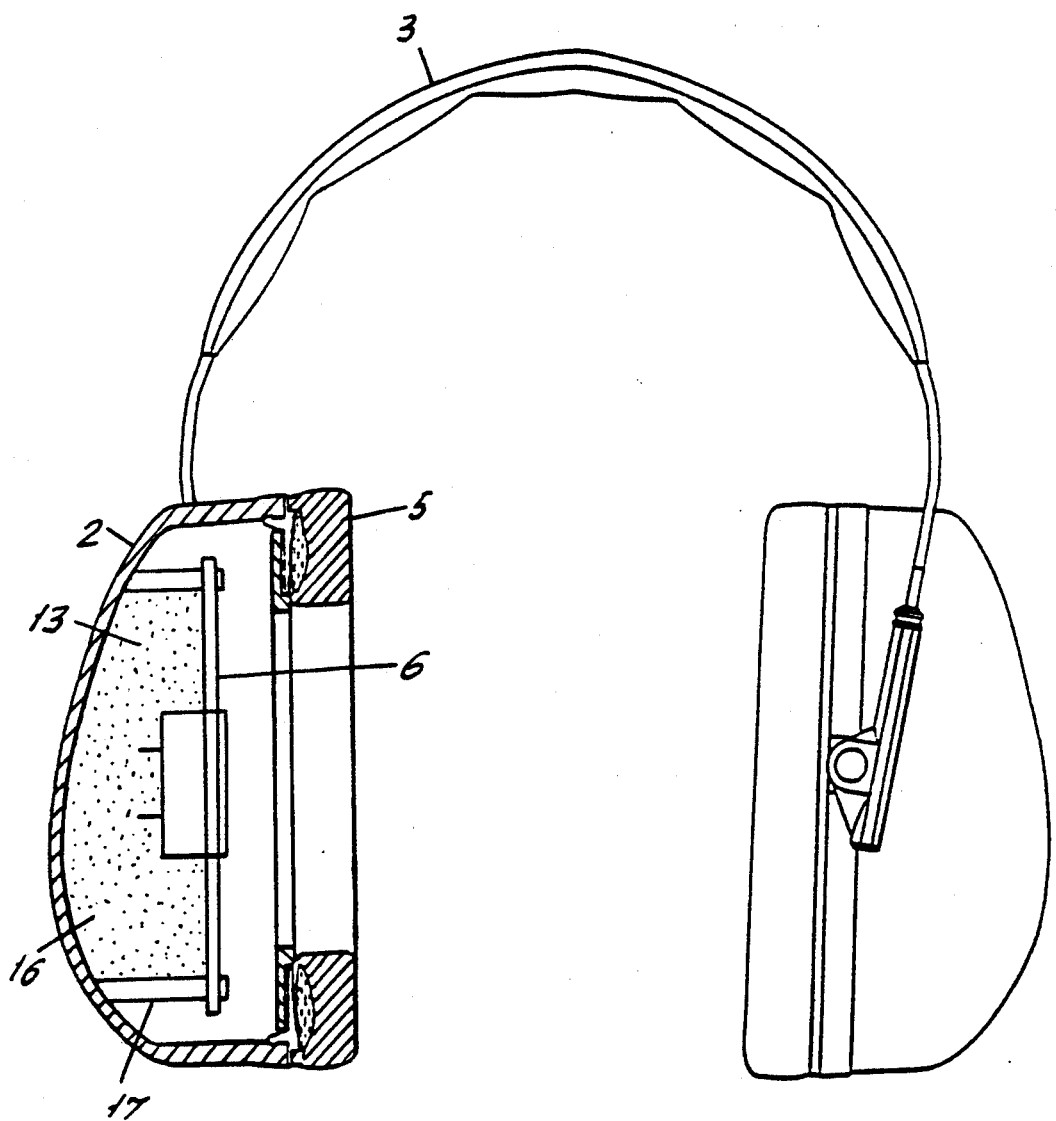
FIG. 3 is a cross-section view of a cup with head phone according to another embodiment of the invention.

FIG. 3 shows a second embodiment of the invention in which, instead of the body 6 illustrated in FIGS. 1 and 2, a substantially flat plate forms the inner wall. This may suitably also carry a head phone 16. The plate 6 may be attached to the outer shell 2 by means of spacers 17. An insert 13 of elastomeric material is similarly arranged in the space between the plate 6 and the outer shell 2 and is compressed between the outer shell 2 and the plate 6. Instead of the through-openings in the cup 6 shown in FIGS. 1 and 2, a sound passage is formed in this embodiment through gaps between the ends of the plate 6 and the outer shell.

The invention can of course be varied in many ways, with the scope of invention being set out by the following claims. The desired sound passage between the two spaces in the ear-protection cup separated by the inner wall, be effected in many other ways besides by means of the openings in the cup 6 shown in FIGS. 1 and 2 and the gaps between the ends of the plate 6 and the outer shell (FIG. 3), in order to achieve a suitable sound passage.

I claim:

1. An ear protection cup for ear muffs or headphones for protecting a user's ear from outside noise, comprising:

an outer frame including a rigid cup-shaped outer shell and a rigid inner wall spaced from said outer shell;

an intermediate space defined by an interior of said outer shell and an exterior of said inner wall;

a layer of elastomeric material disposed within said intermediate space directly contacted and compressed along its entire length by said interior of the outer shell and said exterior of said inner wall, wherein said elastomeric material dampens oscillatory patterns transferred from said outer shell;

means for rigidly connecting said inner wall and said interior of said outer shell; and a resilient sealing member disposed on a peripheral edge of said outer frame for abutting an annular shaped part of the user's head located around the ear.

2. The ear-protection cup of claim 1, wherein the inner wall is provided with a number of through-openings arranged therein.

3. The ear-protection cup of claim 1, wherein said intermediate space has a depth of 1-3 mm.

4. The ear-protection cup of claim 1, wherein said layer of elastomeric material is compressed to less than one half of its thickness in an unloaded state.

5. The ear-protection cup of claim 1, wherein the inner wall consists of a substantially flat wall extending between inner sides of the outer shell.

6. The ear protection cup of claim 1, wherein said inner wall includes stiffening flanges which provide enhanced difference in oscillatory patterns between said outer shell and inner wall.

7. The ear protection cup of claim 1, wherein said connecting means comprise a plurality of spacers.

8. The ear protection cup of claim 1, wherein said outer shell supports a headband of the headphone.

9. An ear protection cup for ear muffs or headphones for protecting a user's ear from outside noise, comprising:

an outer frame including a rigid cup-shaped outer shell and a rigid inner wall spaced from said outer shell;

an intermediate space defined by an interior of said outer shell and an exterior of said inner wall, said intermediate space having a depth of 1 to 3 mm;

a layer of elastomeric material disposed within said intermediate space, directly contacted and compressed along its entire length by said interior of the outer shell and said exterior of said inner wall, wherein said elastomeric material dampens oscillatory patterns transferred from said outer shell;

means for rigidly connecting said inner wall and said interior of said outer shell; and a resilient sealing member disposed on a peripheral edge of said outer frame for abutting an annular shaped part of the user's head located around the ear.

10. The ear-protection cup of claim 1, wherein said layer of elastomeric material is compressed to less than one quarter of its thickness in an unloaded state.

* * * * *